United States Patent
Bourne et al.

(10) Patent No.: US 9,750,638 B2
(45) Date of Patent: Sep. 5, 2017

(54) SYSTEMS AND METHODS FOR OCULAR SURGERY

(71) Applicant: NOVARTIS AG, Basel (CH)

(72) Inventors: John Morgan Bourne, Irvine, CA (US); Glenn Robert Sussman, Laguna Niguel, CA (US)

(73) Assignee: Novartis AG (CH)

( * ) Notice: Subject to any disclaimer, the term of this patent is extended or adjusted under 35 U.S.C. 154(b) by 320 days.

(21) Appl. No.: 14/192,349

(22) Filed: Feb. 27, 2014

(65) Prior Publication Data

US 2014/0271251 A1    Sep. 18, 2014

Related U.S. Application Data

(60) Provisional application No. 61/935,602, filed on Feb. 4, 2014, provisional application No. 61/792,659, filed on Mar. 15, 2013.

(51) Int. Cl.
| | |
|---|---|
| *A61F 9/007* | (2006.01) |
| *F04B 43/12* | (2006.01) |
| *A61M 1/00* | (2006.01) |
| *F04B 43/08* | (2006.01) |

(52) U.S. Cl.
CPC ....... *A61F 9/00745* (2013.01); *A61M 1/0064* (2013.01); *F04B 43/12* (2013.01); *F04B 43/08* (2013.01)

(58) Field of Classification Search
CPC ...... F04B 43/08; F04B 43/12; F04B 43/0072; F04B 43/1215; F04B 43/1253; F04B 43/1261; F04C 2/16; F04C 2/18; F04C 3/02; F04C 3/06; F04C 18/16; F04C 18/084; F04C 2240/20; F04C 2250/20; F04C 2250/201; A61F 9/007; A61F 9/00709; A61F 9/00745; A61F 9/00736;
(Continued)

(56) References Cited

U.S. PATENT DOCUMENTS

| | | |
|---|---|---|
| 121,697 A | 12/1871 | Wheatland |
| 294,334 A | 2/1884 | Reed et al. |
| 351,159 A | 10/1886 | Brengel |

(Continued)

FOREIGN PATENT DOCUMENTS

| | | |
|---|---|---|
| CA | 2316640 | 2/2001 |
| CA | 2649867 A1 | 6/2001 |

(Continued)

OTHER PUBLICATIONS

Kishimoto, Makoto, MD, Opesaver-Super Irrigation System, Techniques in Ophthalmology, 2006, 6 pages, vol. 4, Issue 1, Lippincott Williams & Wilkins, Shiga, Japan.

(Continued)

*Primary Examiner* — Theodore Stigell
*Assistant Examiner* — Chirag Jariwala

(57) ABSTRACT

Ocular surgery may be performed by a variety of systems, processes, and techniques. In certain implementations, a system and a process for ocular surgery may include the ability to draw ocular fluid into a channel of a hand-held pump system and separate the fluid into multiple compressible channels to create multiple flows. The system and the process may also include the ability to peristaltically pump the fluid through the compressible channels.

19 Claims, 4 Drawing Sheets

(58) Field of Classification Search
CPC .............. A61M 1/0058; A61M 1/0064; A61M 1/0066; F01C 5/08
USPC ............... 417/475, 476, 477.4; 418/194, 202
See application file for complete search history.

(56) References Cited

U.S. PATENT DOCUMENTS

| | | | |
|---|---|---|---|
| 865,631 A | 9/1907 | Cotter |
| 1,061,142 A | 5/1913 | Tesla |
| 1,061,206 A | 5/1913 | Tesla |
| 1,874,667 A | 8/1932 | Wada |
| 2,015,123 A | 9/1935 | Pennell |
| 2,121,936 A | 6/1938 | Thomas |
| 2,386,765 A | 10/1945 | Adams et al. |
| 2,536,836 A | 1/1951 | Bowling |
| 2,623,725 A | 12/1952 | Sands |
| 2,755,816 A | 7/1956 | Collins |
| 2,987,004 A | 6/1961 | Murray |
| 3,085,589 A | 4/1963 | Sands |
| 3,191,807 A | 6/1965 | Rodrigues, Jr. |
| 3,336,942 A | 8/1967 | Keith et al. |
| 3,340,817 A * | 9/1967 | Kemnitz ............... F04B 43/12 417/475 |
| 3,447,478 A | 6/1969 | Clemens |
| 3,487,784 A | 1/1970 | Rafferty et al. |
| 3,561,471 A | 2/1971 | Sands |
| 3,567,345 A | 3/1971 | Ballentine |
| 3,589,363 A | 6/1971 | Banko et al. |
| 3,693,613 A | 9/1972 | Kelman |
| 3,724,974 A | 4/1973 | Molimard |
| 3,756,270 A | 9/1973 | Fonseca et al. |
| 3,784,323 A | 1/1974 | Sausse |
| 3,818,913 A | 6/1974 | Wallach |
| 3,882,872 A | 5/1975 | Douvas et al. |
| 3,930,505 A | 1/1976 | Wallach |
| 3,996,935 A | 12/1976 | Banko |
| 4,014,342 A * | 3/1977 | Staub ............... A61F 9/00763 606/170 |
| 4,140,118 A | 2/1979 | Jassawalla |
| 4,187,057 A | 2/1980 | Xanthopoulos |
| 4,205,948 A | 6/1980 | Jones |
| 4,255,081 A | 3/1981 | Oklejas et al. |
| 4,392,794 A | 7/1983 | Foxcroft |
| 4,405,289 A | 9/1983 | Nakashima |
| 4,479,761 A | 10/1984 | Bilstad et al. |
| 4,493,706 A | 1/1985 | Borsanyi et al. |
| 4,496,342 A | 1/1985 | Banko |
| 4,530,647 A | 7/1985 | Uno |
| 4,537,561 A | 8/1985 | Xanthopoulos |
| 4,657,490 A | 4/1987 | Abbott |
| 4,661,093 A | 4/1987 | Beck et al. |
| 4,684,328 A | 8/1987 | Murphy |
| 4,705,500 A | 11/1987 | Reimels et al. |
| 4,713,051 A | 12/1987 | Steppe et al. |
| 4,758,238 A | 7/1988 | Sundblom et al. |
| 4,764,165 A * | 8/1988 | Reimels ............... A61F 9/00736 604/22 |
| 4,768,547 A | 9/1988 | Danby et al. |
| 4,790,726 A | 12/1988 | Balkau et al. |
| 4,798,580 A | 1/1989 | DeMeo et al. |
| 4,838,865 A | 6/1989 | Flank et al. |
| 4,854,825 A | 8/1989 | Bez et al. |
| 4,861,332 A | 8/1989 | Parisi |
| 4,904,238 A | 2/1990 | Williams |
| 4,909,710 A * | 3/1990 | Kaplan ............... F04B 43/082 417/474 |
| 4,909,713 A | 3/1990 | Finsterwald et al. |
| 4,921,477 A | 5/1990 | Davis |
| 4,923,375 A | 5/1990 | Ejlersen |
| 4,935,005 A | 6/1990 | Haines |
| 4,963,131 A | 10/1990 | Wortrich |
| 5,038,965 A | 8/1991 | Cater |
| 5,041,096 A | 8/1991 | Beuchat et al. |
| 5,044,902 A | 9/1991 | Malbec |
| 5,046,486 A | 9/1991 | Grulke et al. |
| 5,062,775 A | 11/1991 | Orth |
| 5,106,366 A | 4/1992 | Steppe |
| 5,106,367 A | 4/1992 | Ureche et al. |
| 5,108,273 A | 4/1992 | Romanyszyn, Jr. |
| 5,167,620 A | 12/1992 | Ureche et al. |
| 5,185,002 A | 2/1993 | Venturini |
| 5,195,960 A | 3/1993 | Hossain et al. |
| 5,207,647 A | 5/1993 | Phelps |
| 5,257,917 A | 11/1993 | Minarik |
| 5,263,830 A | 11/1993 | Goi et al. |
| 5,267,956 A | 12/1993 | Beuchat |
| 5,273,517 A | 12/1993 | Barone et al. |
| 5,302,093 A | 4/1994 | Owens et al. |
| 5,316,440 A | 5/1994 | Kijima et al. |
| 5,340,290 A | 8/1994 | Clemens |
| 5,342,181 A | 8/1994 | Schock et al. |
| 5,350,357 A | 9/1994 | Kamen et al. |
| 5,364,342 A | 11/1994 | Beuchat et al. |
| 5,392,653 A | 2/1995 | Zanger et al. |
| 5,403,277 A | 4/1995 | Dodge et al. |
| 5,429,485 A | 7/1995 | Dodge |
| 5,429,601 A | 7/1995 | Conley et al. |
| 5,429,602 A | 7/1995 | Hauser |
| 5,443,370 A | 8/1995 | Wang |
| 5,460,490 A | 10/1995 | Carr et al. |
| 5,462,416 A | 10/1995 | Dennehey et al. |
| 5,470,312 A | 11/1995 | Zanger et al. |
| 5,476,448 A | 12/1995 | Urich |
| 5,484,239 A | 1/1996 | Chapman et al. |
| 5,487,747 A | 1/1996 | Stagmann et al. |
| 5,515,930 A | 5/1996 | Glaser |
| 5,518,378 A | 5/1996 | Neftel et al. |
| 5,533,976 A | 7/1996 | Zaleski et al. |
| 5,542,918 A | 8/1996 | Atkinson |
| 5,554,013 A | 9/1996 | Owens et al. |
| 5,575,632 A | 11/1996 | Morris et al. |
| 5,588,815 A | 12/1996 | Zaleski et al. |
| 5,630,711 A | 5/1997 | Luedtke et al. |
| 5,674,226 A | 10/1997 | Doherty et al. |
| 5,688,112 A * | 11/1997 | Garay ............... F04B 43/1215 417/477.1 |
| 5,697,910 A | 12/1997 | Cole et al. |
| 5,705,018 A | 1/1998 | Hartley |
| 5,709,539 A | 1/1998 | Hammer et al. |
| 5,712,543 A | 1/1998 | Sjostrom |
| 5,733,256 A | 3/1998 | Costin |
| 5,746,708 A | 5/1998 | Giesler et al. |
| 5,746,719 A | 5/1998 | Farra et al. |
| 5,759,017 A | 6/1998 | Patton et al. |
| 5,782,634 A | 7/1998 | Lingenhöle et al. |
| 5,788,667 A | 8/1998 | Stoller |
| 5,810,765 A | 9/1998 | Oda |
| 5,827,218 A | 10/1998 | Nguyen et al. |
| 5,853,386 A | 12/1998 | Davis et al. |
| 5,879,363 A | 3/1999 | Urich |
| 5,897,300 A | 4/1999 | Luedtke |
| 5,897,524 A | 4/1999 | Wortrich et al. |
| 5,906,598 A | 5/1999 | Giesler et al. |
| 5,910,110 A | 6/1999 | Bastable |
| 5,927,956 A | 7/1999 | Lim et al. |
| 5,951,581 A | 9/1999 | Saadat et al. |
| 5,972,012 A | 10/1999 | Ream et al. |
| 5,989,212 A | 11/1999 | Sussman et al. |
| 5,996,634 A | 12/1999 | Dennehey et al. |
| 5,997,499 A | 12/1999 | Sussman et al. |
| 6,012,999 A | 1/2000 | Patterson |
| 6,042,586 A | 3/2000 | Kawano et al. |
| 6,058,779 A | 5/2000 | Cole |
| 6,080,128 A | 6/2000 | Sussman et al. |
| 6,109,895 A | 8/2000 | Ray et al. |
| 6,110,162 A | 8/2000 | Sussman et al. |
| 6,117,149 A | 9/2000 | Sorensen et al. |
| 6,129,699 A | 10/2000 | Haight et al. |
| 6,179,805 B1 | 1/2001 | Sussman et al. |
| 6,217,543 B1 | 4/2001 | Anis et al. |
| 6,241,700 B1 | 6/2001 | Leukanech |
| 6,270,326 B1 | 8/2001 | Kuriyama |
| 6,293,926 B1 | 9/2001 | Sorensen |
| 6,296,460 B1 | 10/2001 | Smith |

(56) References Cited

U.S. PATENT DOCUMENTS

| | | | |
|---|---|---|---|
| 6,416,293 B1 | 7/2002 | Bouchard et al. | |
| 6,491,661 B1 | 12/2002 | Boukhny et al. | |
| 6,527,765 B2 | 3/2003 | Kelman et al. | |
| 6,551,080 B2 | 4/2003 | Andersen et al. | |
| 6,572,349 B2 | 6/2003 | Sorensen et al. | |
| 6,599,277 B2 | 7/2003 | Neubert | |
| 6,605,054 B2 | 8/2003 | Rockley | |
| 6,655,934 B2 | 12/2003 | Mittelstein et al. | |
| 6,689,146 B1 | 2/2004 | Himes | |
| 6,723,065 B2 | 4/2004 | Kishimoto | |
| 6,749,403 B2 | 6/2004 | Spencer et al. | |
| 6,811,386 B2 | 11/2004 | Hedington et al. | |
| 6,814,547 B2 | 11/2004 | Childers et al. | |
| 6,868,987 B2 | 3/2005 | Hedington | |
| 6,958,058 B1 | 10/2005 | Hunter, Sr. et al. | |
| 6,962,488 B2 | 11/2005 | Davis et al. | |
| 7,063,688 B2 | 6/2006 | Say | |
| 7,070,574 B2 | 7/2006 | Jackson et al. | |
| 7,144,383 B2 | 12/2006 | Arnett et al. | |
| 7,150,607 B2 | 12/2006 | Pelmulder et al. | |
| 7,189,245 B2 * | 3/2007 | Kaplan | A61F 9/007 606/107 |
| 7,238,164 B2 | 7/2007 | Childers et al. | |
| 7,273,359 B2 | 9/2007 | Blight et al. | |
| 7,276,060 B2 | 10/2007 | Madden | |
| 7,393,189 B2 | 7/2008 | Davis et al. | |
| 7,445,436 B2 | 11/2008 | Mittelstein et al. | |
| 7,540,855 B2 | 6/2009 | Lumpkin et al. | |
| 7,604,610 B2 | 10/2009 | Shener et al. | |
| 7,632,080 B2 | 12/2009 | Tracey et al. | |
| 7,645,127 B2 | 1/2010 | Hagen et al. | |
| 7,655,016 B2 * | 2/2010 | Demarais | A61B 17/320725 604/22 |
| 7,695,242 B2 | 4/2010 | Fuller | |
| 7,758,515 B2 | 7/2010 | Hibner | |
| 7,775,780 B2 | 8/2010 | Hopkins et al. | |
| 7,862,540 B2 | 1/2011 | Dacquay et al. | |
| 7,967,777 B2 | 6/2011 | Edwards et al. | |
| 8,070,712 B2 | 12/2011 | Muri et al. | |
| 8,087,909 B2 | 1/2012 | Shener | |
| 8,162,633 B2 | 4/2012 | Edwards | |
| 8,366,420 B1 * | 2/2013 | Geschwender | F04B 43/086 417/475 |
| 8,579,929 B2 | 11/2013 | Mackool et al. | |
| 8,617,106 B2 | 12/2013 | Zacharias | |
| 9,545,336 B2 * | 1/2017 | Sussman | A61F 9/00745 |
| 2001/0016706 A1 | 8/2001 | Leukanech et al. | |
| 2002/0062105 A1 | 5/2002 | Tanner et al. | |
| 2002/0077587 A1 | 6/2002 | Boukhny et al. | |
| 2003/0108429 A1 | 6/2003 | Angelini et al. | |
| 2003/0199803 A1 | 10/2003 | Robinson et al. | |
| 2004/0122381 A1 | 6/2004 | Arnold | |
| 2004/0253129 A1 | 12/2004 | Sorensen et al. | |
| 2005/0049539 A1 | 3/2005 | O'Hara, Jr. et al. | |
| 2005/0070859 A1 | 3/2005 | Cull et al. | |
| 2005/0100450 A1 | 5/2005 | Bryant et al. | |
| 2005/0271531 A1 | 12/2005 | Brown et al. | |
| 2006/0000925 A1 | 1/2006 | Maher et al. | |
| 2006/0093989 A1 | 5/2006 | Hahn et al. | |
| 2006/0110274 A1 | 5/2006 | Gottschalk | |
| 2006/0122556 A1 | 6/2006 | Kumar et al. | |
| 2006/0245964 A1 | 11/2006 | Koslov | |
| 2006/0253194 A1 | 11/2006 | Dial | |
| 2007/0078370 A1 | 4/2007 | Shener et al. | |
| 2007/0078379 A1 | 4/2007 | Boukhny et al. | |
| 2007/0100316 A1 | 5/2007 | Traxinger | |
| 2007/0135760 A1 | 6/2007 | Williams | |
| 2007/0217919 A1 | 9/2007 | Gordon et al. | |
| 2007/0278155 A1 | 12/2007 | Lo | |
| 2007/0287959 A1 | 12/2007 | Walter et al. | |
| 2008/0097320 A1 | 4/2008 | Moore et al. | |
| 2008/0112828 A1 | 5/2008 | Muri et al. | |
| 2008/0114289 A1 | 5/2008 | Muri et al. | |
| 2008/0114291 A1 | 5/2008 | Muri et al. | |
| 2008/0114301 A1 | 5/2008 | Bandhauer et al. | |
| 2008/0114311 A1 | 5/2008 | Muri et al. | |
| 2008/0114312 A1 | 5/2008 | Muri et al. | |
| 2008/0114372 A1 | 5/2008 | Edwards et al. | |
| 2008/0200878 A1 | 8/2008 | Davis et al. | |
| 2008/0220092 A1 | 9/2008 | Dipierro et al. | |
| 2008/0240951 A1 | 10/2008 | Domash et al. | |
| 2008/0247892 A1 * | 10/2008 | Kawasumi | F04B 43/12 417/476 |
| 2009/0012460 A1 | 1/2009 | Steck et al. | |
| 2009/0035164 A1 | 2/2009 | Edwards | |
| 2009/0060756 A1 | 3/2009 | Jones | |
| 2009/0084718 A1 | 4/2009 | Prisco et al. | |
| 2009/0246035 A1 | 10/2009 | Patzer | |
| 2009/0299272 A1 | 12/2009 | Hopping et al. | |
| 2009/0317271 A1 | 12/2009 | Gill et al. | |
| 2010/0125257 A1 | 5/2010 | Perkins et al. | |
| 2010/0130920 A1 | 5/2010 | Lo et al. | |
| 2010/0130934 A1 | 5/2010 | Rochat | |
| 2010/0145259 A1 | 6/2010 | Nash et al. | |
| 2010/0191178 A1 | 7/2010 | Ross et al. | |
| 2010/0228146 A1 | 9/2010 | Hibner | |
| 2010/0241044 A1 | 9/2010 | Caleffi et al. | |
| 2010/0280435 A1 | 11/2010 | Raney et al. | |
| 2010/0286651 A1 | 11/2010 | Sorensen | |
| 2010/0286791 A1 | 11/2010 | Goldsmith | |
| 2011/0092891 A1 | 4/2011 | Gerg et al. | |
| 2011/0137231 A1 | 6/2011 | Sorensen et al. | |
| 2011/0144567 A1 * | 6/2011 | Sorensen | A61F 9/00745 604/22 |
| 2011/0184374 A1 | 7/2011 | Gao et al. | |
| 2012/0041358 A1 | 2/2012 | Mann et al. | |
| 2012/0083728 A1 | 4/2012 | Sorensen et al. | |
| 2014/0163454 A1 * | 6/2014 | Sussman | A61M 1/0031 604/22 |
| 2014/0271273 A1 * | 9/2014 | Carpenter | A61M 1/0064 417/412 |
| 2014/0276364 A1 | 9/2014 | Sussman | |
| 2015/0125328 A1 * | 5/2015 | Bourne | A61F 9/00736 417/477.4 |

FOREIGN PATENT DOCUMENTS

| | | | |
|---|---|---|---|
| CA | 2743969 A1 | 3/2005 | |
| CA | 2649867 C | 6/2010 | |
| CN | 101023898 | 8/2007 | |
| CN | 200991440 Y | 12/2007 | |
| CN | 201133339 Y | 10/2008 | |
| CN | 101541364 A | 9/2009 | |
| DE | 3809582 | 10/1989 | |
| DE | 19749358 | 5/1998 | |
| DE | 19711675 | 10/1998 | |
| DE | 19856744 | 6/2000 | |
| DE | 10034711 B4 | 2/2002 | |
| DE | 10034711 A1 | 4/2006 | |
| DE | 102007044790 | 4/2009 | |
| EP | 0200448 A2 | 11/1986 | |
| EP | 0320963 | 6/1989 | |
| EP | 0362822 A2 | 4/1990 | |
| EP | 518050 A1 | 12/1992 | |
| EP | 518050 B1 | 7/1996 | |
| EP | 0944404 A1 | 9/1999 | |
| EP | 964711 B1 | 12/1999 | |
| EP | 1140257 | 10/2001 | |
| EP | 1258260 A2 | 11/2002 | |
| EP | 1810702 A1 | 7/2007 | |
| EP | 2173404 A1 | 4/2010 | |
| EP | 2365220 | 9/2011 | |
| EP | 2509659 A1 | 10/2012 | |
| FR | 2216840 A5 | 8/1974 | |
| FR | 2466641 | 4/1981 | |
| FR | 2797190 | 2/2001 | |
| GB | 2029514 A * | 3/1980 | F04B 43/12 |
| GB | 2029514 A1 | 3/1980 | |
| GB | 2174763 A * | 11/1986 | F04B 43/12 |
| GB | 2174763 A1 | 11/1986 | |
| GB | 2190145 | 11/1987 | |
| JP | 360001391 A | 7/1985 | |
| JP | 63-290564 | 11/1988 | |

(56) References Cited

FOREIGN PATENT DOCUMENTS

| | | |
|---|---|---|
| JP | 02070987 | 3/1990 |
| JP | H03-164586 | 7/1991 |
| JP | 2002-248117 | 9/2002 |
| JP | 3785643 B2 | 6/2006 |
| JP | 2007-507636 | 3/2007 |
| JP | 2007-198382 | 8/2007 |
| JP | 2007-247646 | 9/2007 |
| JP | 2007263018 A | 10/2007 |
| JP | 2008-546501 | 12/2008 |
| RU | 2067219 C1 | 9/1996 |
| RU | 2197277 | 1/2003 |
| RU | 2241887 | 12/2004 |
| SU | 1533696 A1 | 1/1990 |
| SU | 1590649 A1 | 9/1990 |
| WO | 9517597 | 6/1995 |
| WO | 98/18507 | 5/1998 |
| WO | 98/24495 | 6/1998 |
| WO | 99/38549 | 8/1999 |
| WO | 00/22995 | 4/2000 |
| WO | 00/33898 | 6/2000 |
| WO | 00/53136 | 9/2000 |
| WO | 03073969 A1 | 9/2003 |
| WO | 2005009511 A2 | 2/2005 |
| WO | 2005009511 A3 | 6/2005 |
| WO | 2008/062025 A1 | 5/2008 |
| WO | 2008/131357 | 10/2008 |
| WO | 2009/005900 | 1/2009 |
| WO | 2009/146913 A2 | 12/2009 |
| WO | 2009/146913 A3 | 2/2010 |
| WO | 2010/061863 | 6/2010 |
| WO | 2010/129128 | 11/2010 |
| WO | 2011/071775 | 6/2011 |
| WO | 2012048261 A2 | 4/2012 |
| WO | 2012048261 A3 | 6/2012 |

OTHER PUBLICATIONS

Written Opinion of the International Searching Authority, PCT/US2009/057675, Mar. 25, 2011, 5 pages.
International Preliminary Report of the International Searching Authority, PCT/US2010/041786, Oct. 28, 2010, 5 pages.
Written Opinion of the International Searching Authority, PCT/US2010/041786, Oct. 28, 2010, 7 pages.
International Preliminary Report on Patentability and Written Opinion of the International Searching Authority, issued for International Application No. PCT/US2010/059032, 6 pages.
International Preliminary Report on Patentability and Written Opinion issued for PCT/US2010/058931, dated Feb. 1, 2011, 5 pages.
International Report on Patentability and Written Opinion of the International Searching Authority, International Application No. PCT/2014/027233, dated Sep. 15, 2015, 8 pages.
International Preliminary Report on Patentability, PCT/US2013/064202, issued Jun. 16, 2015.
Extended European Search Report, Application No. 13863111.4, dated Jul. 14, 2015, 6 pgs.
International Preliminary Report on Patentability and Written Opinion of the International Searching Authority, International Application No. PCT/US2014/027307, dated Sep. 15, 2015, 5 pages.
International Preliminary Report on Patentability and Written Opinion of the International Searching Authority, International Application No. PCT/2014/027271, dated Sep. 15, 2015, 6 pages.
International Search Report and Written Opinion issued for PCT/US2014/064416 dated Feb. 18, 2015, 11 pages.
International Search Report and Written Opinion of the International Searching Authority, International Application No. PCT/2015/026293, dated Jul. 23, 2015, 10 pages.
International Searching Report of the International Searching Authority, PCT/US2015/037783, mailed Sep. 28, 2015, 4 pages.
Written Opinion of the International Searching Authority, PCT/US2015/037783, mailed Sep. 28, 2015, 5 pages.
International Search Report for PCT/US2010/058931, filed Dec. 3, 2010, Publication No. 2011071775, Published Jun. 16, 2011, 2 pages.
Written Opinion of the International Searching Authority, International Application No. PCT/US2010/058931, Feb. 1, 2011, 4 pages.
International Search Report for PCT/US2010/059032, filed Dec. 6, 2010, Publication No. 2011075332, Published Jun. 23, 2011, 2 pages.
Written Opinion of the International Searching Authority, International Application No. PCT/US2010/059032, Jan. 31, 2011, 5 pages.
(Citing Office Action), Non-Final Office Action, U.S. Appl. No. 12/637,886, Oct. 3, 2011, 11 pages.
Supplementary European Search Report for Application No. EP 10836456.3, Publication No. EP 2509659, Published Oct. 17, 2012, dated Mar. 20, 2013, 5 pages.
Supplementary European Search Report for Application No. EP 10838118.7, Publication No. EP2512554, Published Oct. 24, 2012, dated Apr. 15, 2013, 6 pages.
Milutinovic, et al., "Phacoemulsification Fluidics System Having a Single Pump Head," U.S. Appl. No. 12/818,682, filed Jun. 18, 2010, 28 pages.
International Searching Authority, Written Opinion of the International Searching Authority, International Application No. PCT/US2010/030168, Aug. 3, 2010, 8 pages.
International Search Report and Written Opinion of the International Searching Authority, International Application No. PCT/US2014/027271, filed Mar. 14, 2014, dated Jul. 28, 2014, 8 pages.
International Search Report and Written Opinion of the International Searching Authority, International Application No. PCT/US2014/027233, filed Mar. 14, 2014, dated Jul. 31, 2014, 10 pages.
International Search Report and Written Opinion of the International Searching Authority, International Application No. PCT/US2014/027307, filed Mar. 14, 2014, dated Jul. 30, 2014, 7 pages.
Sorensen, Gary, Phacoemulsification Hand Piece with Integrated Aspiration Pump, U.S. Appl. No. 13/325,549, filed Dec. 14, 2011, 18 pages.
http://www.advancedfluid.com/discflo/concepts.htm. Web archive dated Aug. 8, 2008, 3 pages.
Ovchinnikov et al., Acoustic Streaming of a Sharp Edge, Journal of Acoustical Society of America, 136 (1), Jul. 2014, pp. 22-29.
Extended European Search Report for Application No. EP 14768258.7, Publication No. EP2941565, Published Nov. 11, 2015, dated Mar. 1, 2016, 8 pages.

* cited by examiner

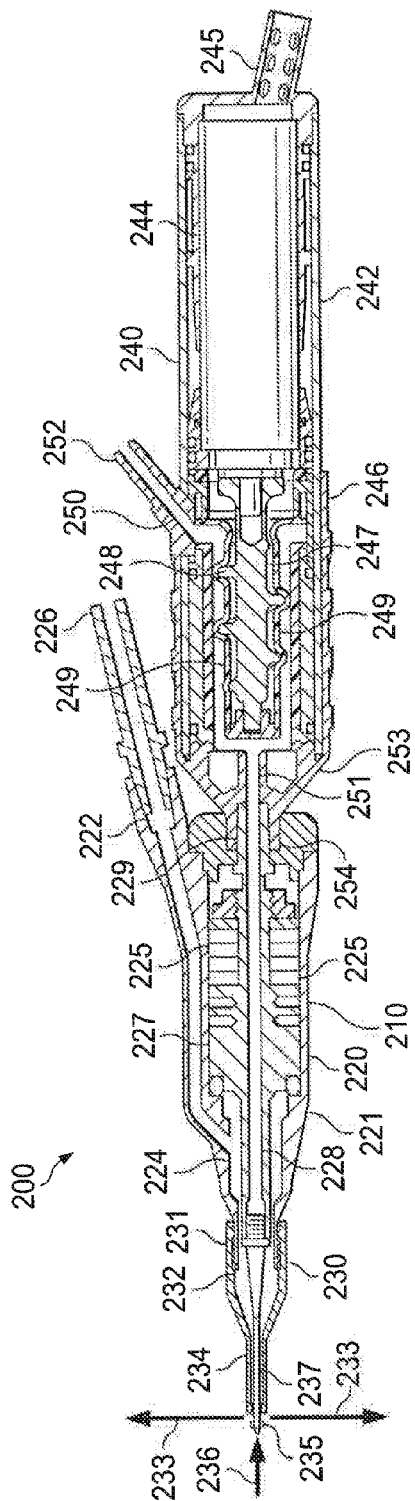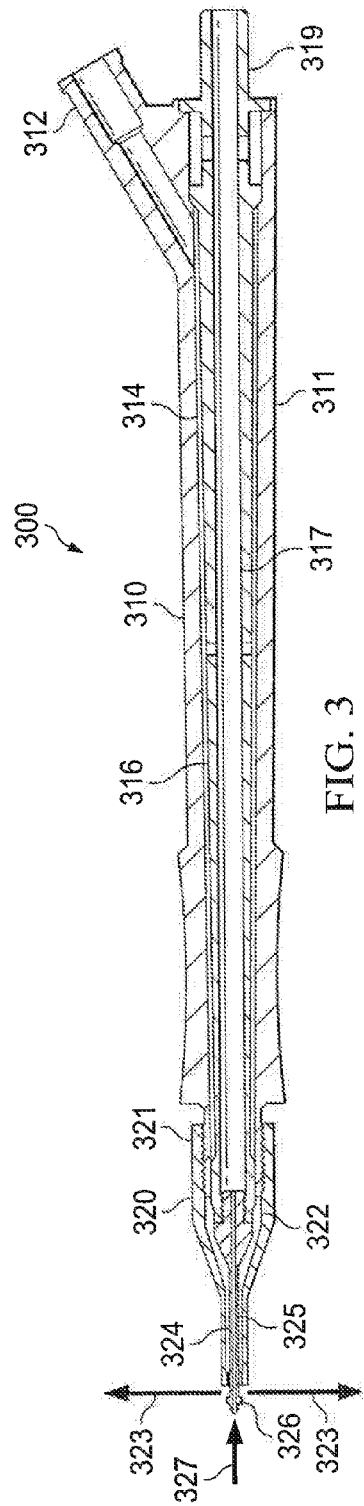
FIG. 2
FIG. 3

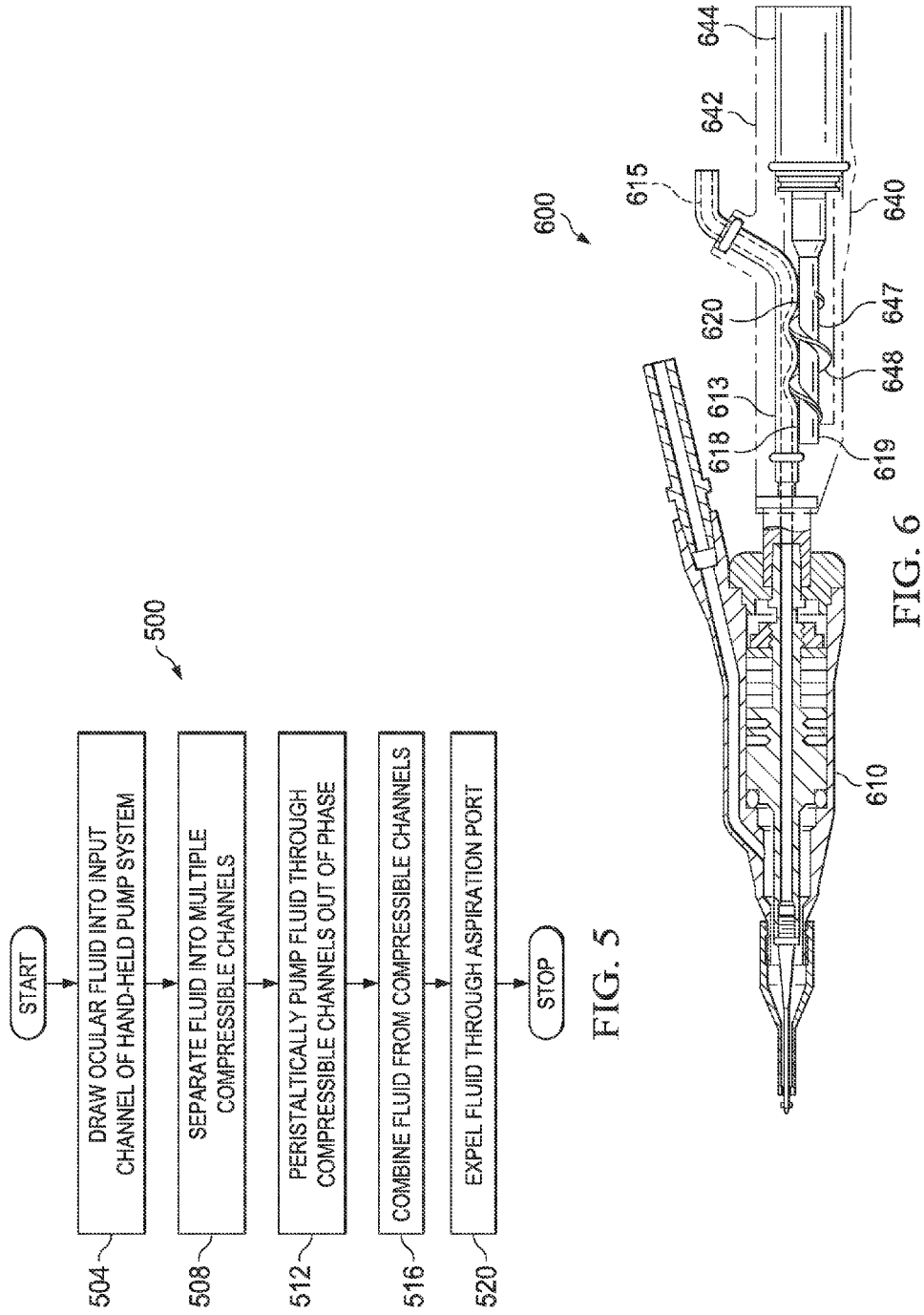

SYSTEMS AND METHODS FOR OCULAR SURGERY

CROSS-REFERENCE TO RELATED APPLICATIONS

This application claims the benefit of U.S. Provisional Application No. 61/792,659, filed Mar. 15, 2013, the entire contents of which are incorporated herein by reference.

TECHNICAL FIELD

The present disclosure relates to ocular surgery, and more specifically to surgical replacement of a patient's lens.

BACKGROUND

The human eye, in simple terms, functions to provide vision by transmitting and refracting light through a clear outer portion called the cornea and focusing the image by way of the lens onto the retina at the back of the eye. The quality of the focused image depends on many factors including the size, shape, and length of the eye, and the shape and transparency of the cornea and lens.

When trauma, age, or disease causes the lens to become less transparent, vision deteriorates because of a reduction in light transmitted to the retina. This deficiency in the eye's lens is medically known as a cataract. The treatment for this condition is often surgical removal of the lens and implantation of an artificial lens, typically known as an intraocular lens (IOL).

An IOL is often foldable and inserted into the eye through a relatively small incision by being advanced through an IOL insertion cartridge, which causes the IOL to fold. The IOL is typically advanced through the insertion cartridge by a plunger-like device.

Before inserting an IOL, the old lens is usually removed through a process called phacoemulsification. In phacoemulsification, an eye's lens is emulsified with an ultrasonic handpiece and aspirated from the eye. Aspirated fluids are replaced with an irrigation of balanced salt solution, thus maintaining the anterior chamber, as well as cooling the handpiece. The irrigation fluid and the aspiration suction are usually supplied by a remote surgical console, which is coupled to the handpiece through several feet of tubing.

Typically, a second stage is required to completely remove the lens, as the first stage only extracts the main portions. Thus, after phacoemulsification, an irrigation-aspiration probe is used to aspirate out the remaining peripheral cortical matter, while leaving the posterior capsule intact.

SUMMARY

A variety of systems, processes, and techniques for ocular surgery are disclosed. In certain implementations, a hand-held pump system for ocular surgery may include a channel adapted to receive a fluid and separate it into at least two compressible channels to create multiple flows and a rotor having a helical scroll. The helical scroll may include a first portion having an increasing radius along a first length of the rotor in the direction of fluid flow. The radius may increase from a first end of the rotor to a maximum value. The helical scroll may also include a second portion having a constant radius along a second length of the rotor. The helical scroll is adapted to compress the compressible channels in a peristaltic manner to capture and move fluid along the channels.

In particular implementations, the helical scroll is adapted to capture fluid in the compressible channels in an out-of-phase manner. The helical scroll may, for example, be adapted to compress the compressible channels in at least two locations to capture fluid.

The second length of the rotor corresponds to a length over which the helical scroll makes at least one rotation around the rotor. In certain implementations, the helical scroll may include a third portion having a decreasing radius along a third length of the rotor, the radius of the third portion decreasing from the maximum value in the direction of fluid flow. The first portion of the rotor may be longer than the second portion of the rotor.

The system may also include a channel coupled to the compressible channels and adapted to receive pumped fluid therefrom. The system may further include an aspiration port adapted to expel the pumped fluid.

In certain implementations, a process for ocular surgery may include drawing ocular fluid into a channel of a hand-held pump system and separating the fluid into multiple compressible channels to create multiple flows. The process may also include peristaltically pumping the fluid through the compressible channels.

In certain implementations, peristaltically pumping the fluid may include compressing each of the compressible channels in at least two locations to capture fluid. The fluid may be captured in the compressible channels in an out-of-phase manner.

In some implementations, peristaltically pumping the fluid may include rotating a rotor having a helical scroll. The helical scroll may include a first portion having an increasing radius along a first length of the rotor in the direction of fluid flow. The radius may increase from a first end of the rotor to a maximum value. The helical scroll may also include a second portion having a constant radius along a second length of the rotor. The helical scroll is adapted to compress the compressible channels in a peristaltic manner to capture and move fluid along the channels. Peristaltically pumping the fluid further may, for example, include compressing the compressible channels in at least two locations with the helical scroll to capture fluid. The fluid may be captured in the compressible channels in an out-of-phase manner with the helical scroll.

The process may also include expelling fluid through an aspiration port. In certain implementations, the process may include combining the fluid from the compressible channels before expelling the fluid through the aspiration port.

Various implementations may have one or more features. For example, since the pump system is hand-held, it may be located nearer to an endpiece (e.g., a phacoemulsification unit and/or an irrigation-aspiration unit), which may improve ocular chamber stability. As another example, the multiple compressible channels may reduce backflow turbulence, making it easier for a user (e.g., a physician or other medical professional) to aspirate fluid from an eye. When turbulence is too high, the material to be aspirated does not easily follow the endpiece.

A variety of other features will be apparent to those skilled in the art from the following description and claims, as well as the accompanying drawings.

BRIEF DESCRIPTION OF THE DRAWINGS

FIG. 2 shows a cross-section view of an example hand-held system for ocular surgery.

FIG. 3 is shows cross-section of an example irrigation-aspiration unit for a hand-held ocular surgery system.

FIG. 5 is a flowchart illustrating an example process for ocular surgery.

FIG. 6 is cross-sectional view of another example hand-held pump system.

DETAILED DESCRIPTION

Figure 1:
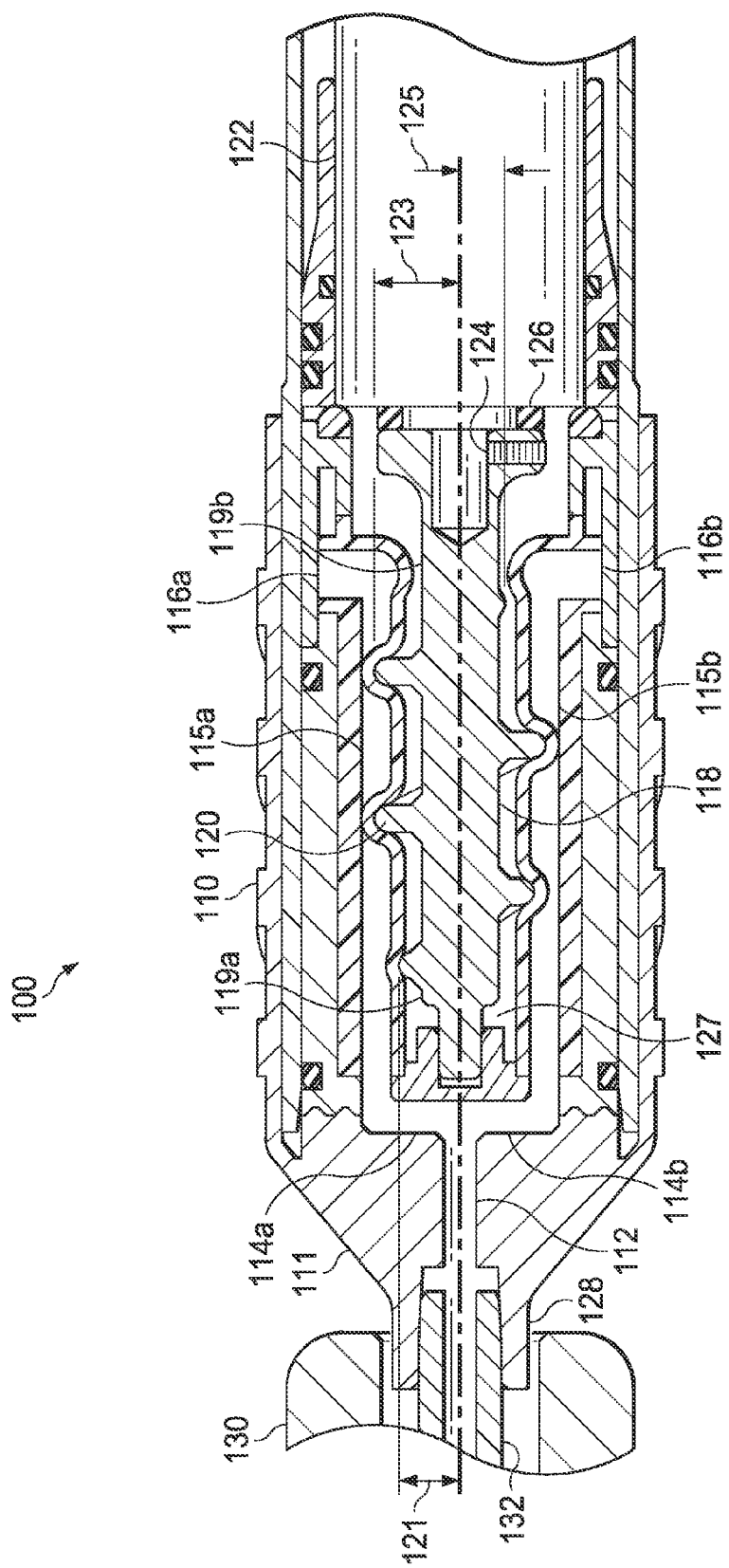
FIG. 1 shows a cross-section view of an example hand-held pump system for ocular surgery.

FIG. 1 illustrates an example hand-held pump system 100 for ocular surgery. Pump system 100 is illustrated as being coupled to an endpiece 130. FIG. 1 illustrates a portion of the endpiece 130 while showing details of pump system 100. The endpiece 130 will be discussed in more detail below. Endpiece 130 may, for example, be a phacoemulsification unit or an irrigation-aspiration unit.

Pump system 100 includes a housing 110. Housing 110 may, for example, be formed from a rigid plastic (e.g., polycarbonate), metal, or any other appropriate material. At a first end 111, housing 110 includes a channel 112 for receiving a fluid to be pumped. The fluid to be pumped may generally be composed of liquids (e.g., aqueous humor and/or water/saline solution) and eye tissue (e.g., emulsified lens portions, cortical matter, and epithelial cells). Channel 112 divides into two channels 114a, 114b. Thus, a portion of the received fluid enters channel 114a, and a portion of the received fluid enters channel 114b. The peripheries of channels 114a, 114b may be composed of the same material as housing 110. Each of channels 114a, 114b is coupled to a respective channel 115a, 115b. Channels 115a, 115b may be composed of a compressible material. Channels 115a, 115b may, for example, be composed of silicone or any other flexible elastomeric material. Channels 115a, 115b are coupled to respective outlet ports 116a, 116b. In the illustrated implementation, conduits (not viewable) carry the fluid from each outlet port 116a, 116b to a side of the pump system 100, where the conduits join and the fluid exits through an aspiration port, an example of which will be discussed below.

Pump system 100 also includes a rotor 118. Rotor 118 may, for example, be made of metal, hard plastic, or any other appropriate type of material. Rotor 118 is generally an elongated member and includes a helical scroll 120 that wraps around the longitudinal axis of the rotor 118. The helical scroll 120 includes a radius measured, for example, from a longitudinal axis of the rotor. The radius of the helical scroll 120 may vary along the length of the rotor. Thus, the helical scroll 120 may include different portions having different radii. In the illustrated implementation, helical scroll 120 has a first radius 121 at a first end 119a of rotor 118 and increases in radius as the helical scroll moves down rotor 118 until a second radius 123 is reached. In some instances, the first radius 121 may be less than the second radius 123. Further, in some implementations, the second radius 123 may be a maximum radius of the helical scroll 120. In some instances, this maximum radius of the helical scroll 120 may be maintained along a first length of the rotor 118 that corresponds to at least one revolution of the helical scroll 120 around rotor 118. The radius of helical scroll 120 may also taper as it approaches a second end 119b of rotor 118. For example, the radius of the helical scroll 120 may decrease along a second length of the rotor 118 proximate the second end 119b of the rotor 118. For example, in some instances, the radius of the helical scroll 120 along the second length of the rotor 118 proximate the second end 119b of the rotor 118 may taper to a radius 125. Further, in some instances, the taper of the helical scroll 120 proximate the first end 119a may be more abrupt than the taper of the helical scroll 119b at the second end 119b. In some instances, the lengths of the rotor 118 over which the helical scroll 120 tapers at the ends 119a, 119b may be substantially the same. In other instances, the length of the rotor 118 over which the helical scroll 120 tapers at the second end 119b may be longer than the length of the rotor 118 over which the helical scroll 120 tapers at the first end 119a.

In operation, rotor 118 is rotated about its longitudinal shaft and thereby rotates helical scroll 118. In FIG. 1, rotor 118 would rotate in a clockwise direction when looking at the rotor from end 119a. As helical scroll 120 is rotates, the helical scroll 118 compresses the channels 115a, 115b such that fluid is captured and transported longitudinally between adjacent peaks of the helical scroll 120 in each of the channels 115a, 115b. In some instances, the channel 115a, 115b may be substantially compressed (i.e., opposite walls of the channels 115a, 115b are made to touch) such that the helical scroll 120 completely partitions portions of the channels 115a, 115b to prevent the fluid from escaping. FIG. 1 illustrates channel 115a as being completely partitioned by adjacent peaks of the helical scroll 120. With fluid captured between two points, continued rotation of helical scroll 120 moves the fluid toward an outlet port 116a, 116b due to the progression of the helical scroll along the longitudinal axis of rotor 118.

In some instances, the channels 115a, 115b may not be substantially compressed at two locations by the helical scroll 120 to capture fluid therein at the same time. The example shown in FIG. 1 illustrates such an example. In some instances, compression of the channels 115a, 115b may be 180 degrees out of phase. That is, when helical scroll 120 is capturing an amount of fluid in one of the channels 115a or 115b by compressing the channel at two points (as is occurring in channel 115a, shown in FIG. 1), the helical scroll 120 is not capturing fluid in channel 115b. Thus, helical scroll 120 alternates between capturing fluid in each of channels 115a, 115b. By alternating the capturing of fluid between channels 115a, 115b, pulses, which may create backflow turbulence in the fluid, may be reduced.

In some instances, the length of the rotor 118 at the first end 119a over which the radius of helical scroll 120 increases to a maximum value may be such that the radius gradually increases. For example in some instances, this length may correspond to one revolution of the helical scroll 120 about the rotor 118. The gradual increase in the radius of the helical scroll 120 reduces the compression rate of the channels 115a, 115b, thereby reducing the magnitude of the fluid backflow pulses. The length of the rotor 118 over which the radius of the helical scroll 120 decreases near end 119b may be relatively short as any turbulence created at this location of the rotor 118 is not translated back towards the eye.

Pump system 100 also includes a motor 122 to drive rotor 118. Motor 122 may, for example, be an electrical motor, and power for the electrical motor may be received through a conduit. Motor 122 may, for example, be a direct current (DC) motor. In certain modes of operation, motor 122 may drive rotor 118 at several thousand revolutions per minute (RPM). In some instances, the motor 122 may be coupled to rotor 118 by a set screw 124. However, in other implementations, other couplings may be used.

Pump system 100 also includes a seal 126. Seal 126 prevents lubricating fluid in a chamber 127 for rotor 118 from leaking out of the pump system 100 during operation of the pump system 100. Chamber 127 is separate from the fluid pathway(s) conducting fluid to a patient, such as channels 115a, 115b.

At first end 111, housing 110 includes a female luer fitting 128. Female luer fitting 128 may be sized to accept a male luer fitting 132 of endpiece 130. In some instances, the luer fittings are mated by a friction fit. Thus, endpiece 130 may be detachable from pump system 100. Other matings (e.g., threaded) could be used in other implementations. Moreover, an endpiece 130 could be permanently attached to a pump system 100. Male luer fitting 132 includes a channel 134 through which fluid is aspirated from an eye. The fluid is conveyed through channel 134 to channel 112 due to the pumping action of pump system 100.

Pump system 100 has a variety of features. For example, locating the pump system 100 nearer to an endpiece 130 (e.g., a phacoemulsification unit and/or an irrigation-aspiration unit) may improve chamber stability. Maintaining a steady intraocular pressure in the eye is important because pressure fluctuations can result in, among other things, posterior capsule rupture, endothelial cell loss, and inflammation. Improved anterior chamber stability should produce improved clinical outcomes. As another example, reducing backflow turbulence may make it easier for a user (e.g., a physician or other medical professional) to aspirate fluid from the eye. When turbulence is too high, the material to be aspirated will not easily follow the endpiece. Previous attempts at implementing such a pump have resulted in unwanted pulsations, which create turbulence in the eye and make it difficult to aspirate materials therefrom. These pulsations also occur in surgical consoles, but their effect is dampened significantly due to the length of the conduit (e.g., tubing) through which the fluid is pulled (e.g., 6 feet). Moreover, a pump in a surgical console typically is larger, which allows for spreading out the period of the individual pulses.

Additionally, since endpiece 130 is detachable from pump system 100, another endpiece may be coupled to pump system 130. For example, a phacoemulsification handpiece may first be coupled to pump system 100 and then an irrigation-aspiration handpiece may be coupled to the pump system. Thus, pump system 100 may be used for a variety of operations during a surgical procedure.

Although FIG. 1 illustrates an example pump system 100, other pump systems may include fewer, additional, and/or a different arrangement of components. For example, a pump system may include more than two compressible channels. This may increase flow rate and/or decrease pulsation. As another example, the length of the rotor 118 over which the radius of helical scroll 120 increases may be shorter or longer. As an additional example, helical scroll 120 may make multiple rotations around rotor 118 at the maximum radius. As another example, a different coupling may be used for the endpiece 130. As a further example, channel 112 and/or channels 114 may also be composed of a compressible material. As another example, a handheld pump system 100 may not include a motor. For example, a motor could be located remotely (e.g., on a surgical console) and coupled to the rotor (e.g., via a torque transmission wire). As an additional example, the out-of-phase fluid capture may be performed using fluid channels that have different inner diameters, thereby compressing out-of-phase.

FIG. 2 illustrates an example system 200 for ocular surgery. System 200 includes a phacoemulsification unit 210 and a pump unit 240 that are detachably coupled together. In general, phacoemulsification unit 210 is adapted to fragment an eye's lens into pieces and aspirate the pieces with the suction provided by pump unit 240, which is similar to pump system 100.

Phacoemulsification unit 210 includes a body portion 220 and a tip portion 230. Body portion 220 includes a housing 221 that is substantially rigid and may be made of hard plastic, metal, or any other appropriate material. Body portion 220 may be any length, but is typically between about 4-6 inches in length. Body portion 220 also includes an infusion port 222 for receiving infusion fluids (e.g., a water/saline solution) for delivery to an eye during a lens fragmentation and removal process. The fluid may, for example, be provided by a surgical console or a stand-alone irrigation supply line. Infusion port 222 empties into a channel 224 inside of housing 221.

Body portion 220 also includes resonators 225. Resonators 225 are adapted to generate high-frequency vibrations (e.g., ultrasonic) in response to applied electrical power, which may be received through an electrical conduit 226. In particular implementations, resonators 225 may be piezoelectric transducers.

Internal to housing 221, body portion 210 includes a horn 227 that is vibrated by resonators 225. Horn 227 may, for example, be composed of metal. Horn 227 includes a channel 228 through which eye fluid and tissue may be aspirated. Horn 227 also includes a male luer fitting 229. In particular implementations, male luer fitting 229 may be formed from a polymer, which may facilitate resisting separation from pump unit 240 due to the vibrations of system 200 during use. In other implementations, male luer fitting 229 may be composed of a metal or any other appropriate material.

Tip portion 230 includes a sleeve 231 that is flexible. Sleeve 231 may, for example, be made of an elastomeric material (e.g., silicone). Sleeve 231 defines a channel 232 into which the fluid in channel 224 flows. The fluid may flow through channel 232 until it exits tip portion 230, as indicated by arrows 233.

Tip portion 230 also includes a surgical tip 234 located in the center thereof. Tip 234 is engaged with horn 227 of body portion 220 and receives vibrations from resonators 225 therethrough. Tip 234 may, for example, be made of metal (e.g., stainless steel or titanium). Tip 234 includes a distal section 235 that may be activated against a lens to emulsify the lens. Distal section 235 of tip 234 includes a port (not viewable) into which fluid in the eye (e.g., aqueous humor and/or fluid irrigating the eye), as well as eye tissue (e.g., lens portions), may be aspirated from the eye, as indicated by arrow 236. The fluid may be conveyed down a lumen 237 defined by the tip 234, which communicates with channel 228 of body portion 220.

In the illustrated implementation, tip portion 230 engages with body portion 220 via threads. In other implementations, a barbed or interference fit may be used.

Pump unit 240 includes a body 242 that may be made of metal, hard plastic, or any other appropriate material. Body 242 may be any length, but is typically between about 4-6 inches. Body 242 houses, among other things, a motor 244 that produces a rotational drive motion. In some implementations, the motor 244 is an electric motor and produces a rotational drive motion in response to supplied electrical power, which is received through electrical conduit 245. In particular implementations, motor 244 may be a direct current (DC) motor. In other implementations, the motor 244 may be pneumatic or hydraulic. In still other implementations, the motor 244 may be any suitable device operable to generate a rotation drive motion.

Pump unit 240 also includes a pump 246 that is driven by motor 244. As illustrated, pump 246 is a scroll-type peristaltic pump. Pump 246 includes a rotor 247 that has a helical scroll 248 wound around the longitudinal axis of the rotor 247. The helical scroll 248 has a radius that increases from the end of the helical scroll 248 nearest phacoemulsification unit 210 to a maximum radius. The maximum radius may be maintained for a length along the rotor 247 corresponding to one to four revolutions of the helical scroll 248 about the rotor 247. The radius of the helical scroll 248 may then decrease at an opposite end of the rotor 247. Pump 246 also includes a compressible material 249 that defines multiple conduits (not seen in this view) adapted to convey fluid. The conduits may be similar to the channels 115*a*, 115*b* shown in FIG. 1. The conduits in compressible material 249 are not viewable because of the nature of the location of the cross-sectional cut defining FIG. 2. For example, the cross-sectional view shown in FIG. 2 is at 90 degrees to the cross-sectional cut shown in FIG. 1. However, FIG. 2 does show a conduit 250 to which the outlet ports for pump 246 are coupled. A conduit similar to conduit 250 is not viewable in FIG. 1. Conduit 250 thus collects fluid from the conduits in compressible material 249 and conveys them to an aspiration port 252.

In operation, pump 246 draws fluid and any eye tissue through a channel 251 that is in communication with channel 228. The fluid is drawn through the system 200 as a result of compression of the compressible material 249 by helical scroll 248. The fluid is then collected in conduit 250 and conveyed to aspiration port 252 through which aspirated fluid may be discharged. The aspirated material (e.g., fluid and tissue) may be conveyed to a container (e.g., a bag or tank) for holding biologic material.

Pump unit 240 also includes an adapter 253 coupled to the end the pump unit 240 nearest phacoemulsification unit 210. Adapter 253 includes a female luer fitting 254 that is adapted to receive male luer fitting 229 of phacoemulsification unit 210. The two luer fittings mate with each other and may be retained due to a friction fit. Female luer fitting 254 may, for example, be made of metal (e.g., stainless steel or titanium), plastic, or any other appropriate material.

In operation, one or more incisions are made in the eye to allow the introduction of surgical instruments. The user (e.g., physician or other medical professional) then removes the anterior face of the capsule that contains the lens inside the eye.

Distal section 235 of tip portion 230 may then be inserted into the eye through one of the incisions. The distal section 235 may be brought into contact with the lens. Resonators 225 may then be activated at a relatively high frequency (e.g., ultrasonic), causing distal section 235 to vibrate. As a result, the lens is fragmented and emulsified. The pump unit 240 aspirates fluid and the emulsified lens particles through the tip 234. In some instances, the lens is broken into two to four pieces, and each piece is emulsified and aspirated out with suction through lumen 237, channel 228, channel 251, and aspiration port 252. After removing the hard central lens nucleus with phacoemulsification, the softer outer lens cortex may be removed exclusively with suction (e.g., with an irrigation-aspiration unit).

System 200 has a variety of features. For example, locating the pump unit nearer to an endpiece (e.g., phacoemulsification unit and/or irrigation-aspiration unit) may improve chamber stability. That is, the benefits of the present disclosure include improved intraocular pressure stability within the anterior chamber of the eye. Also, the present disclosure provides for reduced pulsation in the fluid flow and, therefore, reduced fluid turbulence in the eye. As a result, the present disclosure provides for improved aspiration of materials from the eye.

Additionally, since phacoemulsification unit 210 is detachable from pump unit 240, another unit may be coupled to pump unit 240. For example, an irrigation-aspiration probe or a vitrectomy probe may be coupled to the pump unit. Thus, system 200 provides a modular design and provides the ability to use pump unit 240 for a variety of operations during a procedure.

Although FIG. 2 illustrates one example system for ocular surgery, other systems for ocular surgery may include fewer, additional, and/or a different arrangement of components. For example, a different phacoemulsification unit may be used with pump unit 240. Thus, pump unit 240 is adaptable to different phacoemulsification units. For instance, in some implementations, a phacoemulsification unit may include a second fine metal instrument called a "chopper" that is used from a side port to help with chopping the nucleus into smaller pieces. As another example, a different pump unit may be used with phacoemulsification unit 210 having a fitting adapted to mate with the fitting of the phacoemulsification unit 210.

As an additional example, phacoemulsification unit 210 may also be used with a standard surgical console. Because phacoemulsification unit 210 includes male luer fitting 229, it may readily couple to surgical conduits (e.g., hoses or tubes) to a surgical console.

Although male luer fitting 229 and female luer fitting 254 are shown to be mated by a friction fit, different types of couplings may be used. For example, female luer fitting 254 may have threads on an interior surface thereof that intermesh with corresponding threads on male luer fitting 229. Thus, a friction fit and a threading engagement may mate pump unit 240 with phacoemulsification unit 210. In particular implementations, pump unit 240 may be mated with phacoemulsification unit 210 through a threading engagement without a luer fitting. Various other couplings operable to maintain phacoemulsification unit 210 and pump unit 240 in an integrated hand-held configuration during a procedure are also within the scope of the present disclosure.

FIG. 3 illustrates an example irrigation-aspiration unit 300. Irrigation-aspiration unit 300 may, for example, be used with a pump system similar to pump system 100.

Irrigation-aspiration unit 300 includes a body portion 310 and a tip portion 320. Body portion 310 includes a housing 311 that is substantially rigid and may be made of hard plastic, metal, or any other appropriate material. Body portion 310 also includes an infusion port 312 for receiving infusion fluids, such as, for example, a water/saline solution (e.g., a balanced salt solution), for delivery to an eye during an ocular procedure, such as, for example, an eye cleaning and/or polishing process. The fluid may, for example, be supplied from a surgical console. Infusion port 312 empties into a channel 314 inside of housing 311.

Internal to housing 311, body portion 310 includes a conduit 316. In some instances, conduit 316 may, for example, be composed of hard plastic. Conduit 316 defines a channel 317 through which fluid, along with other materials, may be aspirated.

Body portion 310 also includes a fitting 319. In some instances, the fitting 319 may be a male luer portion. In particular implementations, the fitting 319 is composed of a polymer. In other implementations, the fitting 319 may be composed of a metal or any other appropriate material. The fitting 319 is operable to couple the irrigation-aspiration unit 300 to a hand-held pump system.

Tip portion 320 includes a sleeve 321 that is flexible. Sleeve 321 may, for example, be made of an elastomeric material (e.g., silicone). The sleeve 321 defines a channel 322 that communicates with channel 314. Thus, channel 322 is operable to convey fluid from the channel 314. The fluid flow through channel 322 and exits the tip portion 320, as indicated by arrows 323.

Tip portion 320 also includes a conduit 324 that extends through the channel 322 of the sleeve 321. Conduit 324 defines a channel 325 that communicates with the channel 317 of conduit 316. Fluid and other materials aspirated from the eye are conveyed along channel 325 and into the channel 317. Conduit 324 may, for example, be made of stainless steel or titanium.

A tip 326 is coupled to an end of conduit 324. Tip 326 includes a port (not viewable) into which fluid in the eye (e.g., aqueous humor and/or fluid irrigating the eye) as well as tissue (e.g., cortical material and epithelial cells) may be aspirated from the eye, as indicated by arrow 327. The fluid and other materials may be conveyed through channel 325 and channel 317. Tip 326 may, for example, be made of a polymer, silicone, or other appropriate material.

In the illustrated implementation, the sleeve 321 of the tip portion 320 slideably engages with body portion 310. In other implementations, a barbed or threaded engagement may be used.

In operation, irrigation-aspiration unit 300 may be coupled to a handheld pump system, such as a pump system similar to the pump system 100 or pump unit 240, described above. The irrigation-aspiration unit 300 may also be coupled to an irrigation supply line. The supply line may be coupled to a surgical console. Tip 326 of tip portion 320 may be inserted into the eye through an incision. Cortical material may be aspirated, along with other tissue (e.g., epithelial cells), while leaving the posterior capsule intact. Simultaneously, fluids may be irrigated into the eye, for example, to maintain stability of the eye. Additionally, if desired, the posterior capsule of the eye may be polished with tip 326.

Irrigation-aspiration unit 300 may include a variety of features. For example, by allowing a pump unit to be located nearer to the irrigation-aspiration unit 300, anterior chamber stability is improved. Further, reduced fluid pulsation and turbulence associated therewith is reduced.

Additionally, since irrigation-aspiration unit 300 is detachable from a pump unit, another unit may be coupled to the pump unit. For example, a phacoemulsification probe or a vitrectomy probe may be coupled to the pump unit. Thus, irrigation-aspiration unit 300 provides the ability to use a pump unit with a variety of different instruments, thereby permitting the irrigation-aspiration unit 300 to be used in a variety of surgical procedures or different operations or steps within a single surgical procedure. Additionally, irrigation-aspiration unit 300 may be used with a conventional surgical console if desired.

Although FIG. 3 illustrates an example irrigation-aspiration unit 300, other systems may use other irrigation-aspiration units may include fewer, additional, and/or a different arrangement of components.

Figure 4A:
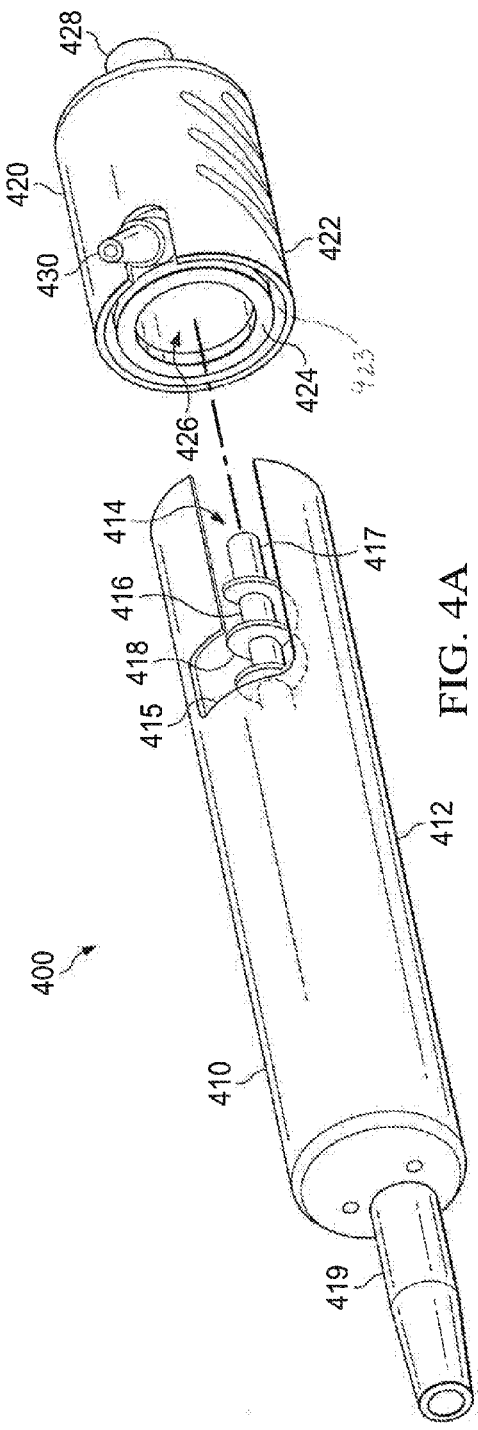
FIG. 4A shows another example hand-held pump system for ocular surgery.
Figure 4B:
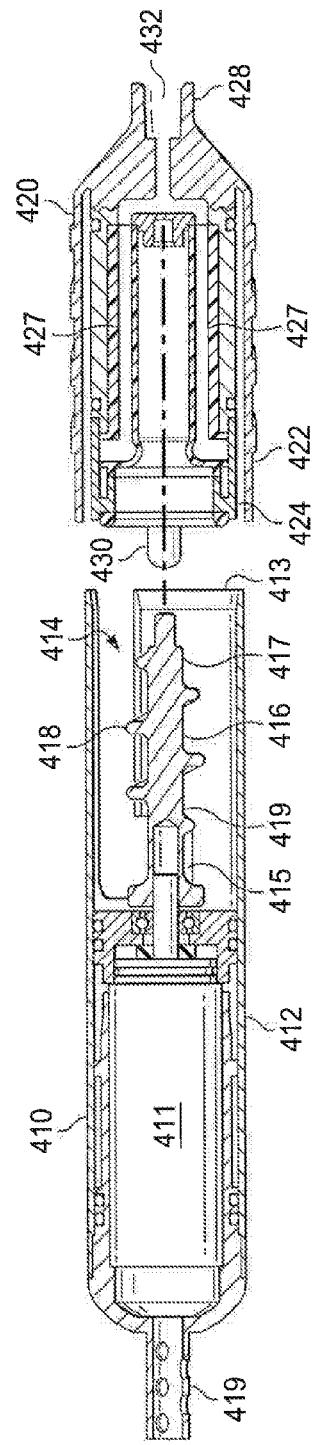
FIG. 4B shows an exploded cross-sectional view of the hand-held pump system of FIG. 4A.

FIGS. 4A and 4B illustrate another example pump system 400. Pump system 400 includes a drive portion 410 and a pumping portion 420. Pump system 400 may, for example, be usable in system 200 or for use with irrigation-aspiration unit 300.

Drive portion 410 includes a body 412. In the illustrated implementation, body 412 is generally cylindrical and may be made of metal. However, in other implementations, the body 412 may have other shapes and be made of other materials. Body 412 includes a slot 414 for receiving a portion of pumping portion 420, to be discussed below. An electric motor 411 is disposed within the body 412. The electric motor 411 is coupled and operable to rotate a rotor 416.

Rotor 416 includes a helical scroll 418 that winds around the rotor 416 along a longitudinal axis thereof. In the illustrated implementation, helical scroll 418 has a smaller radius at a first end 417 of rotor 416. The radius increases along a length of the rotor 416 until it reaches its maximum radius. The portion of the helical scroll 418 having the maximum radius may extends along a length of the rotor 416. For example, the maximum radius may exist for at least one revolution of the helical scroll 418 around rotor 416. Along another length of the rotor 416, the radius of helical scroll 418 may decrease proximate a second end 419 of rotor 416. Power is supplied to the drive portion 410 through a conduit 419.

Pumping portion 420 includes an outer shell 422 and an inner shell 424. A slot 423 is formed between the inner shell 422 and the outer shell 424. Outer shell 422 is sized to fit around body 412 of drive portion 412, and inner shell 424 is sized to fit inside body 412. Thus, body 412 slides between outer shell 422 and inner shell 424. The shells may be made of hard plastic, metal, or any other appropriate material. Inside inner shell 424, pumping portion 420 includes a number of compressible conduits 426 that includes integrated conduits 427. In a manner similar to that described above, helical scroll 418 of rotor 416 engages compressible conduits 426 such that material in the integrated conduits 427 is transported therethrough in a peristaltic manner. For example, the rotor 416 may compress the elastomeric pump section 426, thereby causing a peristaltic pumping action to transport material within the integrated conduits 427. The drive portion 410 is coupled to the rotor 416 and is operable to rotate the rotor 416.

Pumping portion 420 also includes a fitting 428 that is configured to engage a corresponding fitting on an endpiece (e.g., a phacoemulsification unit and/or an irrigation-aspiration unit). In other implementations, the fitting 428 may be adapted to be received into a female fitting on a unit, such as a phacoemulsification hand piece, and irrigation and aspiration hand piece, or any other desired device. Fitting 428 includes an interior channel 432. The interior channel 432 is in fluid communication with the integrated conduits 427. Fluid may be drawn into pump system 400 through the interior channel 432. Pumping portion 420 also includes a fluid port 430 through which fluid may be expelled from pump system 400.

The drive portion 410 and the pumping portion 420 may be coupled together by insertion of a distal end 413 of the body 412 into the slot 423 and between the outer shell 422 and the inner shell 424 of the pumping portion 420 with the fluid port 430 aligned with the slot 414. Fluid port 430 is sized to be received in slot 414 in body 412. In the illustrated example, the pumping portion 420 may be rotated relative to the drive portion 410 such the fluid port 430 resides within a transverse portion 415 of the slot 414. By rotating fluid port 430 in slot 414, the fluid port 430 is made to reside in the transverse portion 415 of slot 414, causing the pumping portion 420 to be secured to drive portion 410.

Pump system 400 has a variety of features. For example, pump system 400 allows pumping action to be performed near an endpiece. Thus, the stability of the anterior chamber of the eye may be improved. Additionally, since pumping portion 420 is separable from drive portion 410, pumping portion 420 may be removed after a procedure (e.g., due to being contaminated with biological material) while preserving drive portion 410. Thus, drive portion 410 may be used for multiple procedures. Generally, the drive portion 410 would be sterilized between procedures for different patients. Additionally, since fitting 428 is configured to engage a number of endpieces (e.g., a phacoemulsification unit and an irrigation-aspiration unit), pump system 400 may be used for numerous types of surgical procedures and/or for different operations of a single surgical procedure.

FIG. 6 illustrates another example pump 600. The system 600 may be similar to the system 200 described herein and includes a phacoemulsification unit 610 and a pump unit 640. The pump unit 640 may be similar to pump system 100 and pump unit 240, described above, except that the pump unit 640 includes a single flexible conduit 613. The pump unit 640 is shown in FIG. 6 coupled to a phacoemulsification unit 610. The phacoemulsification unit 610 may be substantially the same as the phacoemulsification unit 210, described above. Therefore, the description of the phacoemulsification unit 210 applies equally to the phacoemulsification unit 610 and, thus, will not be repeated.

The pump unit 640 includes a body 642 and a motor 644 housed within the body 642. The motor 644 may be similar to the motor 244, described above. The pump unit 640 also includes the flexible conduit 613 defining a channel 615. The flexible conduit 613 may be formed from silicone or any other flexible elastomeric material. The pump unit 640 also includes a rotor 647, similar to the rotors 118 and 247. The rotor 647 includes a helical scroll 648, which also may be similar to the helical scrolls 120 and 248. Thus, in some instances, the helical scroll 648 may include a tapered portion such that a radius of the helical scroll 648 increases over a longitudinal length of the helical scroll 648. For example, in a manner similar to helical scroll 120, the helical scroll 648 may include a first portion 618 at a first end 619 that gradually increases until a maximum radius is achieved. The helical scroll 648 may include a second portion 620 that extends along a longitudinally length and includes a constant radius. The constant radius of the second portion 620 may be equal to the maximum radius of the first portion 618.

As explained above with respect to pump system 100, the rotor 647 is disposed adjacent to a length of the flexible conduit 613. In a manner similar to the pump system 100 described above, the helical scroll 648 compresses the flexible conduit 613 as rotor 647 is rotated such that fluid is captured within the conduit 615 between adjacent peaks of the helical scroll 648 and transported along the flexible conduit 613.

FIG. 5 illustrates selected operations for an example process 500 for ocular surgery. Process 500 may, for example, be accomplished with a system similar to system 100, 200, 400, or 600.

Process 500 calls for drawing ocular fluid into an input channel of a hand-held pump system (operation 504). The fluid being pumped may generally be composed of liquids (e.g., aqueous humor and/or water/saline solution) and eye tissue (e.g., emulsified lens portions, cortical matter, and epithelial cells). The hand-held pump system may be permanently or detachably coupled to an endpiece (e.g., a phacoemulsification unit or an irrigation-aspiration unit).

Process 500 also calls for separating the fluid into multiple compressible channels (operation 508). The fluid may, for example, be separated into a plurality of compressible channels. In some instances, the fluid may be separated by conveyance through a T or a Y junction. However, in other implementations, other junctions are possible. The separation may occur before or after the fluid enters a compressible channel. For example, the input channel may be a compressible channel.

Process 500 additionally calls for pumping the fluid through the compressible channels in an out-of-phase peristaltic manner (operation 512). In some instances, the pump should be operable to substantially compress a channel at two points at the same time or substantially the same time to capture a volume of fluid. To pump the channels in an out-of-phase manner, the pump initiates capturing of fluid in the different channels at different times. The pump may, for example, have a helical scroll with having a varying radius along the length thereof.

Process 500 also calls for combining fluid from the compressible channels (operation 516). The fluid from the compressible channels may, for example, be combined by conveying it through a junction. In some instances, the junction may be a T or Y junction.

Process 500 additionally calls for expelling the fluid through an aspiration port (operation 520). The fluid may, for example, by conveyed to a container (e.g., plastic bag).

Although FIG. 5 illustrates one implementation of a process for ocular surgery, other processes for ocular surgery may include fewer, additional, and/or a different arrangement of operations. For example, a process may include operations prior to emulsifying the lens. For example, a process may include detachably coupling the pump system to an endpiece (e.g., a phacoemulsification unit or an irrigation-aspiration unit). As another example, a process may include detachably coupling a pump unit to a motor. As an additional example, a process may include detaching an endpiece and attaching another endpiece. As a further example, the fluid from the compressible channels may not be recombined. For instance, the separated fluid may exit the handheld system through separate aspiration ports. Moreover, a number of the operations may be performed in a contemporaneous or simultaneous manner.

The various implementations discussed and mentioned herein have been used for illustrative purposes only. The implementations were chosen and described in order to explain the principles of the disclosure and the practical application and to allow those of skill in the art to understand the disclosure for various implementations with various modifications as are suited to the particular use contemplated. Thus, the actual physical configuration of components may vary. For example, the mentioned size(s) of components and their illustrated sizing relative to each other may vary based on application. Moreover, the shapes of one or more components may vary depending on application. Thus, the illustrative implementations should not be construed as defining the only physical size, shape, and relationship of components. Further, although the disclosure describes that various pump systems and pump unit as being directed to ocular surgery, the scope of the disclosure is not so limited. Rather, ocular surgery is merely an example, non-limiting application for which such pump units and systems may be used. It is within the scope that such pump systems and units may be utilized for other types of surgeries or in areas completely outside of the medical arts.

Various systems and techniques for ocular surgery have been discussed, and several others have been mentioned or suggested. However, those skilled in the art will readily recognize that a variety of additions, deletions, substitutions, and modifications may be made to these systems and techniques while still achieving ocular surgery. Thus, the scope of protection should be judged based on the following claims, which may capture one or more aspects of one or more implementations.

The invention claimed is:

1. A hand-held pump system, the system comprising:
   a pumping portion comprising:
      a first channel comprising at least two compressible channels, each of the compressible channels adapted to create a separate fluid flow; and
      a fluid port in fluid communication with the two compressible channels; and
   a drive portion comprising:
      a housing;
      a rotor disposed in the housing and having a helical scroll engaged with the compressible channels, the helical scroll comprising:
         a first portion having an increasing radius along a first length of the rotor in the direction of fluid flow, the radius increasing from a first end of the rotor to a maximum value; and
         a second portion having a constant radius along a second length of the rotor, the helical scroll compresses the compressible channels in a peristaltic manner to capture and move fluid along the compressible channels; and
      a slot formed in the housing, the slot including a transverse portion, the fluid port receivable into the slot and secured into the transverse portion of the slot by rotation of the pumping portion relative to the drive portion.

2. The system of claim 1, further comprising a motor adapted to drive the rotor.

3. The system of claim 1, wherein the pumping portion further comprises an outer shell and an inner shell and wherein a distal end of the body is insertable between the outer shell and the inner shell to couple the drive portion and the pumping portion.

4. The system of claim 1, wherein the second length of the rotor corresponds to a length over which the helical scroll makes at least one rotation around the rotor.

5. The system of claim 1, wherein the helical scroll further comprises a third portion having a decreasing radius along a third length of the rotor, the radius of the third portion decreasing from the maximum value in the direction of fluid flow.

6. The system of claim 5, wherein the first portion of the rotor is longer than the second length of the rotor.

7. The system of claim 1, further comprising a second channel coupled to the compressible channels and adapted to receive pumped fluid therefrom.

8. The system of claim 7, further comprising an aspiration port adapted to expel the pumped fluid.

9. The system of claim 1, wherein the helical scroll compresses the compressible channels so as to capture fluid therewithin in an out-of-phase manner.

10. The system of claim 2, wherein the helical scroll compresses the compressible channels in at least two locations to capture fluid.

11. A hand-held pump system, the system comprising:
    a pumping portion comprising:
       an outer shell;
       an inner shell located within the outer shell;
       a slot formed between the outer shell and the inner shell; and
       a first channel comprising at least two compressible channels, each of the compressible channels adapted to create a separate fluid flow;
    a drive portion comprising:
       a housing comprising a distal end, the distal end insertable into the slot between the outer shell and the inner shell to couple the drive portion and the pumping portion;
       a rotor disposed within the housing, the rotor having a helical scroll engaged with the compressible channels, the helical scroll comprising:
          a first portion having an increasing radius along a first length of the rotor in the direction of fluid flow, the radius increasing from a first end of the rotor to a maximum value; and
          a second portion having a constant radius along a second length of the rotor, the helical scroll compresses the compressible channels in a peristaltic manner to capture and move fluid along the compressible channels.

12. The system of claim 11, wherein the second length of the rotor corresponds to a length over which the helical scroll makes at least one rotation around the rotor.

13. The system of claim 11, further comprising a motor adapted to drive the rotor.

14. The system of claim 11, wherein the helical scroll compresses the compressible channels so as to capture fluid therewithin in an out-of-phase manner.

15. The system of claim 14, wherein the helical scroll compresses the compressible channels in at least two locations to capture fluid.

16. The system of claim 11, wherein the helical scroll further comprises a third portion having a decreasing radius along a third length of the rotor, the radius of the third portion decreasing from the maximum value in the direction of fluid flow.

17. The system of claim 16, wherein the first portion of the rotor is longer than the second length of the rotor.

18. The system of claim 11, further comprising a second channel coupled to the compressible channels and adapted to receive pumped fluid therefrom.

19. The system of claim 18, further comprising an aspiration port adapted to expel the pumped fluid.

* * * * *